US005396885A

United States Patent [19]

Nelson

[11] Patent Number: 5,396,885

[45] Date of Patent: Mar. 14, 1995

[54] MOBILE AIR SUPPLY CART HAVING DUAL TANKS AND CONNECTIONS ALLOWING SIMULTANEOUS FILLING OF TANK AND DELIVERY OF AIR TO A USER

[76] Inventor: Joseph M. Nelson, 2416 Wilson Ave., Bristol, Pa. 19007

[21] Appl. No.: 923,311

[22] Filed: Jul. 31, 1992

[51] Int. Cl.[6] ........................ A61M 16/00; A62B 9/02; A62B 18/02; F16L 3/00

[52] U.S. Cl. ........................... 128/204.18; 128/205.24; 128/205.25; 248/122; 248/129; 137/343

[58] Field of Search ....................... 128/200.24, 204.18, 128/205.24, 205.25, 202.22, 202.27, 205.23; 137/259, 262, 265, 376, 343; 248/122, 129

[56] References Cited

U.S. PATENT DOCUMENTS

| | | | |
|---|---|---|---|
| 2,122,897 | 7/1938 | Straw | 128/204.18 |
| 2,667,397 | 1/1954 | Hallisey | 128/204.18 |
| 2,854,001 | 9/1958 | Humblet | 128/202.22 |
| 3,244,196 | 4/1966 | Replogle | 128/202.22 |
| 3,791,403 | 2/1974 | Folkerth | 128/204.18 |
| 4,452,241 | 6/1984 | Sarnoff et al. | 128/204.18 |
| 4,510,930 | 4/1985 | Garcia | 128/202.22 |
| 4,798,203 | 1/1989 | Bartos | 128/205.22 |
| 4,944,292 | 7/1990 | Gaeke et al. | 128/204.18 |
| 5,057,822 | 10/1991 | Hoffman | 128/202.22 |

OTHER PUBLICATIONS

Ohio Chemical, "Oxygen Therapy & Accessories Catalog", 4 sheets, pp. 15 & 28, May 2, 1966, rep. by Airco Co. Int'l, New York, N.Y.

Foregger, "Anesthesia Apparatus", The Foregger Co., Roslyn Heights, N.Y., 1962, Cat. #17, 3 sheets, p. 64.

*Primary Examiner*—Kimberly L. Asher
*Attorney, Agent, or Firm*—Woodcock Washburn Kurtz Mackiewicz & Norris

[57] ABSTRACT

A mobile air supply cart for use by personnel wearing respirators while working in hazardous environments. The cart supports two compressed air cylinders and has a handle and wheels, thereby facilitating transporting the air supply as the movements of the user require. A connector pin allows the cart to be separated into a base assembly and a frame assembly to which the cylinders are secured. In this configuration the cylinders can be carried through confined spaces. A piping system is mounted on the cart and regulates the pressure of the air supplied to the user. Valving allows the cylinder from which air is supplied to be switched out and the other cylinder to be switched in as the air is depleted in one cylinder without interrupting the supply of air to the user. A low pressure manifold on the cart allows several users to be supplied with air simultaneously. A coupling in the piping system allows the cylinders to recharged from a remote air supply while simultaneously supplying air to the user.

9 Claims, 5 Drawing Sheets

MOBILE AIR SUPPLY CART HAVING DUAL TANKS AND CONNECTIONS ALLOWING SIMULTANEOUS FILLING OF TANK AND DELIVERY OF AIR TO A USER

FIELD OF THE INVENTION

The current invention is directed to a mobile air supply cart. More specifically, the current invention is directed to a cart for transporting cylinders that contain a supply of air for personnel using supplied air respirators while working in smoke filled, toxic or otherwise hazardous environments.

BACKGROUND OF THE INVENTION

Typically, personnel working in environments in which the air is unsafe to breath, such as fire fighters or environmental hazard response workers, wear a respirator mask to which air is supplied. With self-contained breathing apparatus, the respirator mask is supplied with air from cylinders carried on the user's back. However, the weight of such cylinders limits the mobility of the wearer and the amount of air that may be carried is limited. Accordingly, such personnel often utilize a supplied air system, in which air is supplied to the respirator mask from a remote source. Stand-alone pressurized air cylinders, such as those used in self-contained breathing apparatus, may be used as such a remote source of air. Unfortunately, such cylinders are heavy and bulky, and transporting them to facilitate movement of the user is difficult and time consuming. This presents a serious drawback in those situations in which the user must move rapidly, a frequent occurrence when fighting fires. In addition, a way must be found to recharge the cylinders without interrupting the supply of breathing air to the user. As a result of these difficulties, the use of compressed air cylinders as a remote source of breathing air has met with limited success.

Consequently, it would be desirable to provide a mobile air supply cart that facilitated use of compressed air cylinders as a remote source of air for personnel working in hazardous environments. Such a cart should be readily transportable, even in confined spaces. In addition, such a mobile air supply cart should allow the cylinders to be recharged without interrupting the supply of air to the user.

SUMMARY OF THE INVENTION

It is an object of the current invention to provide a mobile air supply cart that facilitates the use of compressed air cylinders as a remote source of air for personnel working in hazardous environments, that is readily transportable, even in confined spaces, and that allows the cylinders to be recharged without interrupting the supply of air to the user. This object, as well as other objects, is accomplished in a mobile gas supply cart having a support for supporting at least one compressed gas cylinder. At least one wheel is rotatably coupled to the support and a piping assembly is supported on the support. The piping system has (i) a high pressure manifold supported by the support and having an inlet port for receiving gas from a compressed gas cylinder and an outlet port, (ii) a pressure regulator in flow communication with the high pressure manifold outlet port, and (iii) a low pressure manifold having an inlet port in flow communication with the pressure regulator and at least one outlet port for supplying gas to a gas consumer. The support has (i) a base portion to which the wheel is coupled, (ii) a frame portion for supporting a compressed gas cylinder, and (iii) a connector for coupling and uncoupling the frame portion from the base portion.

In one embodiment of the current invention, the cart has a coupling for receiving compressed gas from a gas supply and the high pressure manifold has a second inlet port in flow communication with the coupling, whereby a compressed gas cylinder supported on the frame may be charged with compressed gas through the high pressure manifold. In addition, the frame has means for supporting two compressed gas cylinders and the piping assembly has means for placing either of the two compressed gas cylinders in flow communication with the high pressure manifold inlet port.

DESCRIPTION OF THE PREFERRED EMBODIMENT

Figure 1:
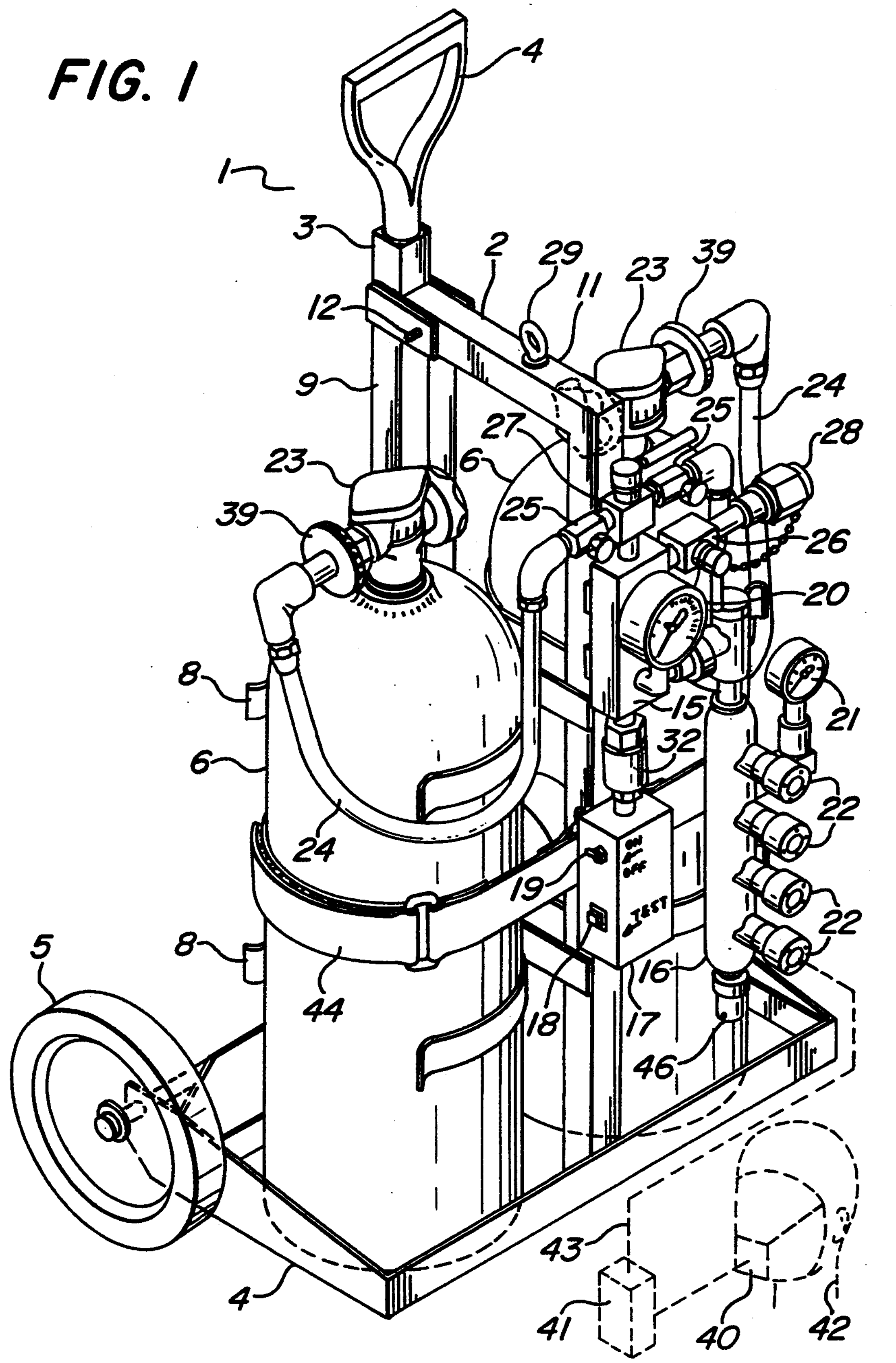
FIG. 1 is an isometric view, from the front, of the mobile air supply cart according to the current invention.
Figure 2:
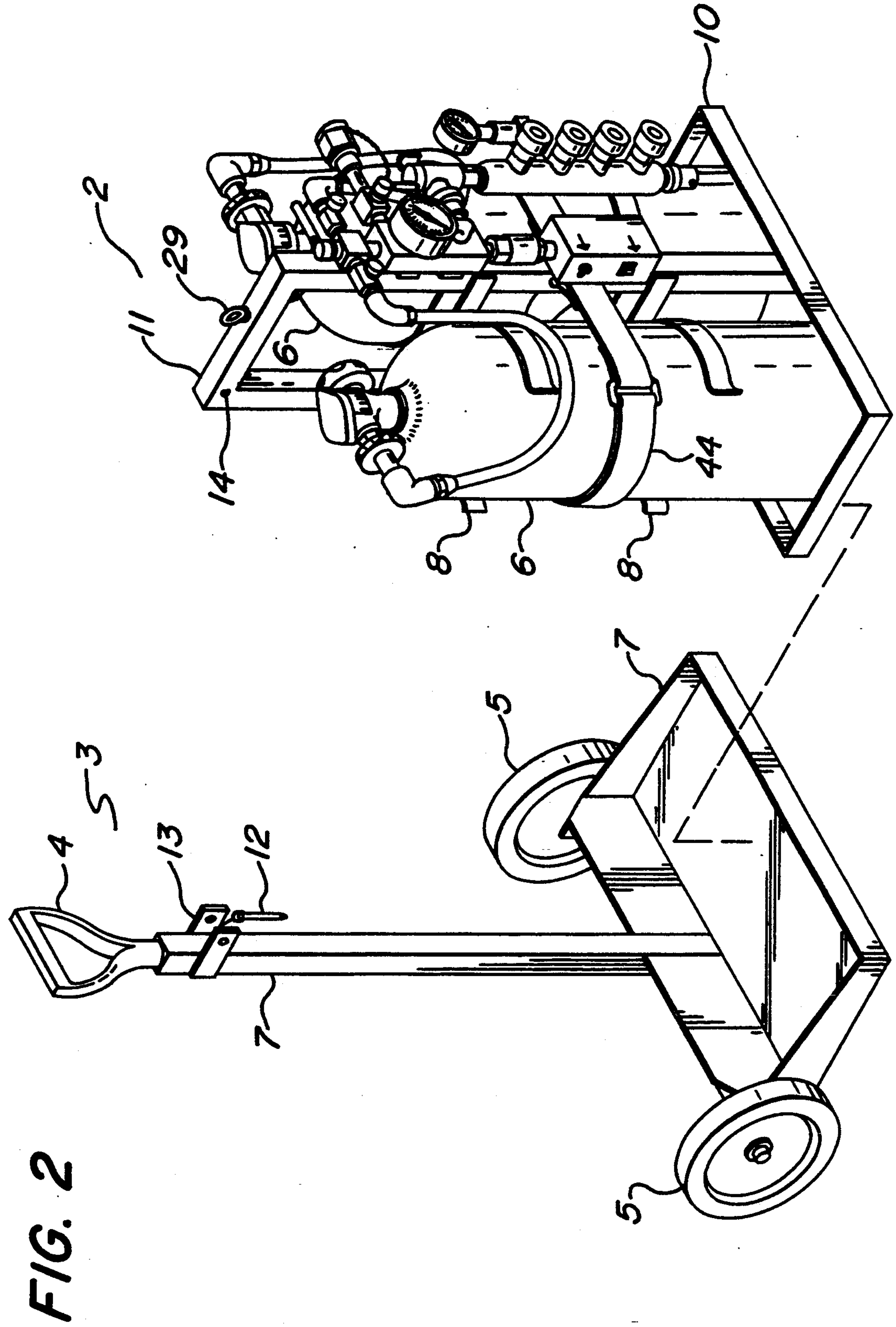
FIG. 2 is an exploded view of the mobile air supply cart showing the frame assembly, with the cylinders installed, removed from the base.
Figure 3:
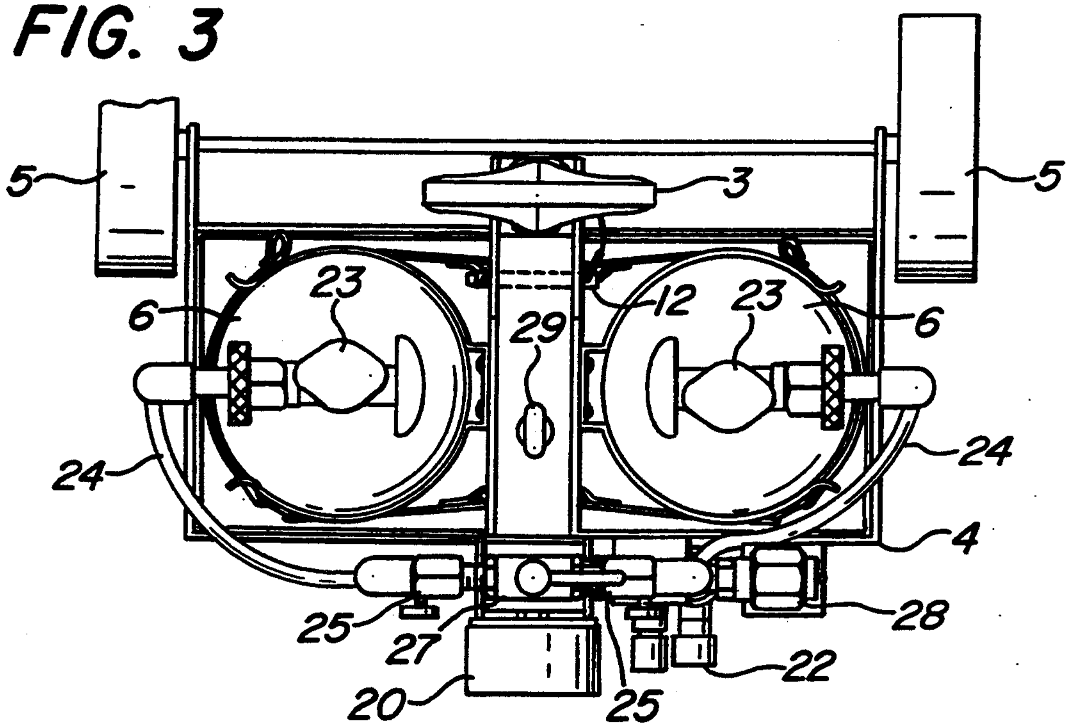
FIG. 3 is a view of the mobile air supply cart from above.

The mobile air supply cart 1 according to the current invention is shown in FIGS. 1–5. As shown in FIG. 1, the cart 1 supplies breathing air to a regulator 41 of a face mask 40 worn by a user 42 working in a hazardous environment. As shown in FIG. 2, the cart 1 is comprised of a frame assembly 2 that is separable from a base assembly 3. The base 3 has a post 9 to which a handle 4 is affixed at one end and a bottom 7 is affixed at the other end. In addition, a pair of wheels 5 are rotatably mounted on the base 3.

The frame 2 has a center support 11 extending upwardly from a tray 10 attached thereto. The tray 10 is adapted to support a pair of compressed air cylinders 6. A pair of clamps 8 and a strap 44 extend from each side of the center support 11 and are adapted to secure the cylinders 6 to the frame. Advantageously, the straps 44 have patches 37 of synthetic material which adhere when pressed together, such as those sold under the trademark VELCRO TM, shown in FIG. 5, that facilitate the rapid change-out of cylinders 6. In addition, the clamps 8 are provided in a number of sizes and each may be readily replaced by removing two screws 45, shown in FIG. 5, that secure the clamp to the frame 2. The use of removable clamps 8 of differing sizes according to the current invention facilitates the use of a variety of cylinders 6.

Figure 4:
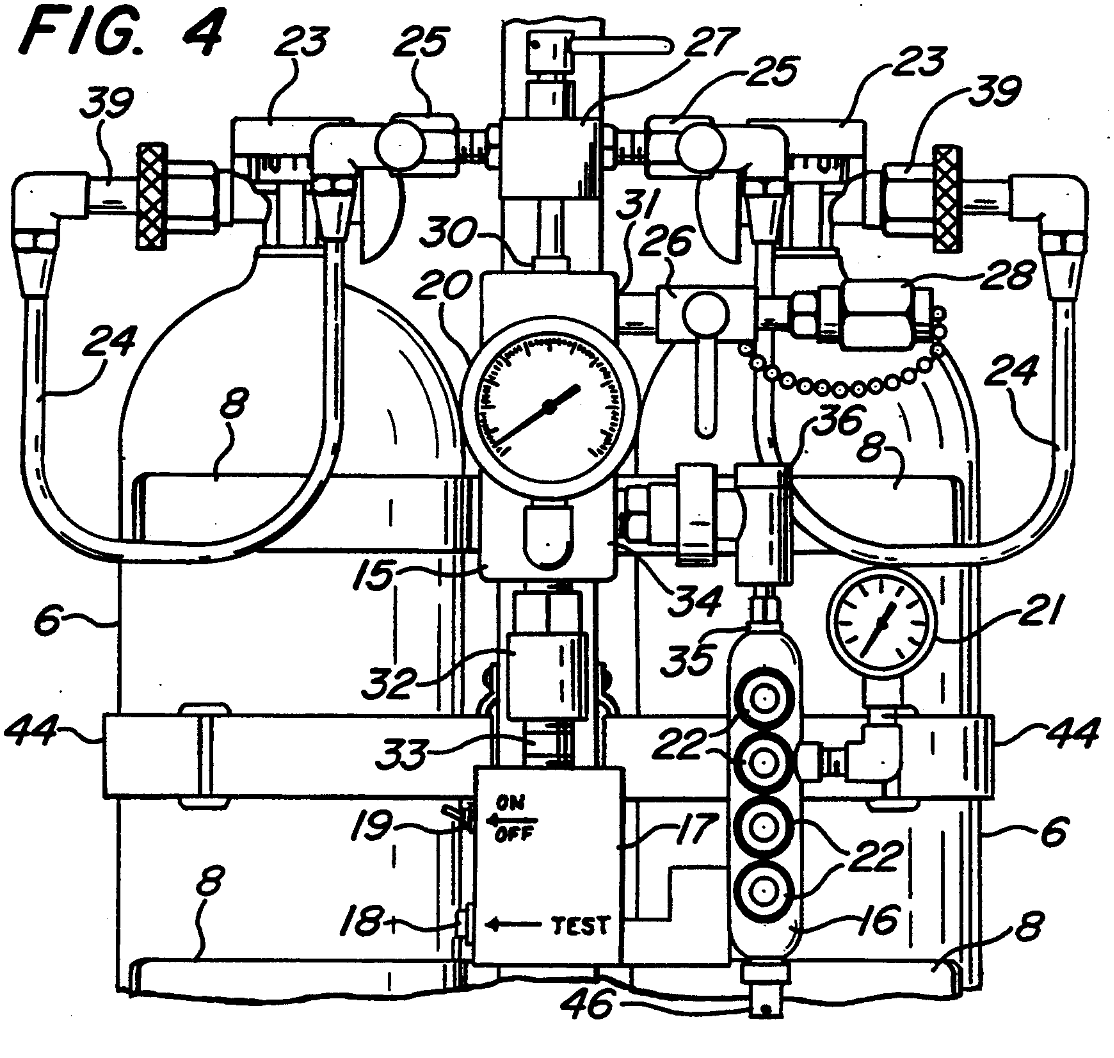
FIG. 4 is detailed view of the piping system for the mobile air supply cart.

A piping system, shown best in FIG. 4, is mounted on the front of the frame 2. The piping system, as discussed further below, regulates the flow of breathing air from the cart 1 to the face mask regulator 41, shown in FIG. 1.

As shown in FIG. 2, the cart base 3 has a collar 13 in which holes are located so as to be aligned with a hole 14 in the center support 11 of the frame 2. A pin 12 is inserted through the holes in the collar 13 and the hole 14 in the frame 2 to lock the two portions of the cart together, as shown in FIG. 1. In the locked-together configuration shown in FIG. 1, the cart 1 allows the air cylinders 6 to be readily transported, via the wheels 5 and handle 4, to facilitate the movement of the user. If, however, it is necessary to transport the air cylinders 6 through very confined spaces, the pin 12 allows the frame 2 to be readily separated from the base 3, as shown in FIG. 2, yielding a very compact configuration that can, for example, be carried through port holes in a ship. A lifting ring 29 mounted in the center support 11 facilitates lifting of the frame assembly 2.

As shown best in FIG. 4, each of the compressed air cylinders 6 has a first shut-off valve 23 at its top. The piping system features a coupling 39 for each cylinder 6 that is adapted to mate with the outlets of the shut-off valves 23. High pressure hoses 24 and second shut-off valves 25 direct the compressed air from the cylinders 6 to a three-way valve 27. From the three-way valve 27, the air flows to an inlet port 30 on a high pressure manifold 15. (It should be understood that the terms "high" and "low" as used herein with respect to pressure are intended to indicate relative values only.) A gauge 20 allows the pressure of the air in the high pressure manifold 15 to be monitored.

From the high pressure manifold 15 the compressed air flows, via an outlet port 34 and a pressure regulator 36, to an inlet port 35 of a low pressure manifold 16. The pressure of the air in the cylinders 6 is typically over 1000 psi. Accordingly, the pressure regulator 36 allows the pressure supplied to the low pressure manifold 16 to be reduced to about 125 psi, a pressure suitable for supplying air to the face mask regulator 41 shown in FIG. 1. A gauge 21 connected to the low pressure manifold 16 allows the pressure of the air in the manifold to be monitored. A safety valve 46 connected to the low pressure manifold 16 ensures that the pressure in the manifold does not exceed a predetermined value.

In the preferred embodiment, the low pressure manifold 16 has four outlet ports 22, each of which includes an ANSI quick disconnect fitting that allows a hose 43 connected to the face mask regulator 41, shown schematically in FIG. 1, to be attached to the low pressure manifold 16. Thus, the cart 1 is capable of simultaneously supplying air to as many as four users.

Figure 5:
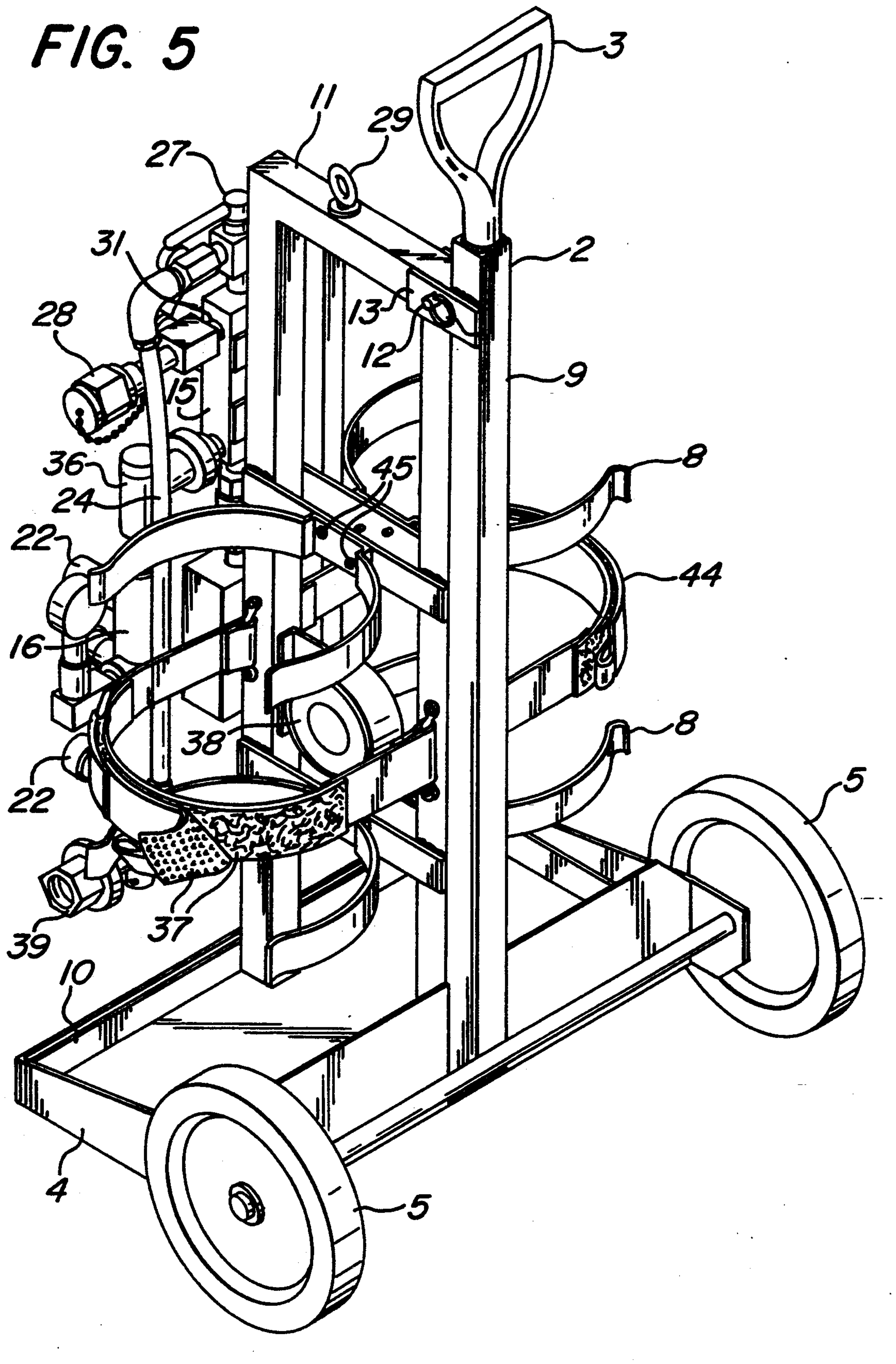
FIG. 5 is an isometric view, from the rear, of the mobile air supply cart with the cylinders removed.
Figure 6:
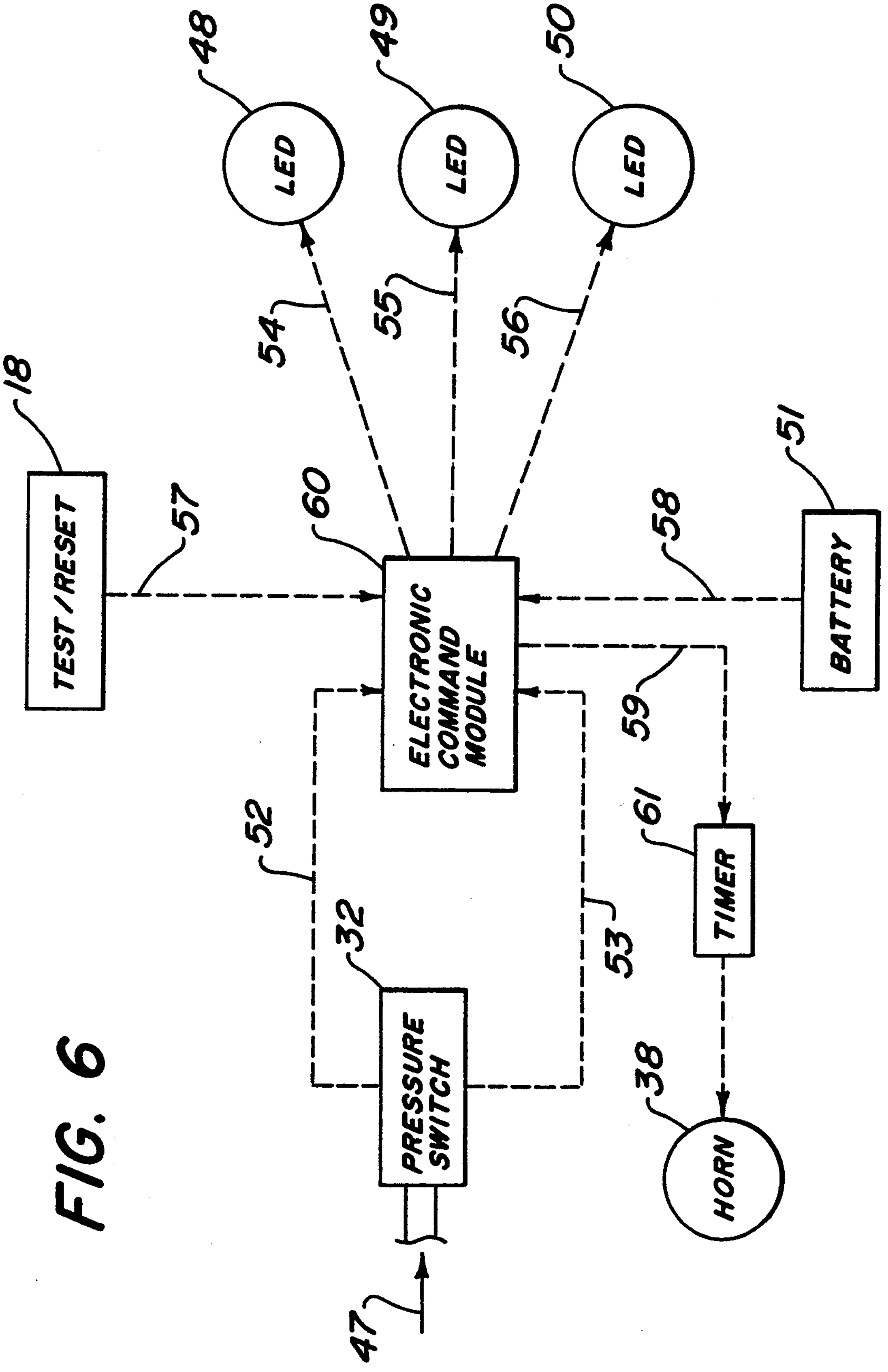
FIG. 6 is a schematic diagram of a monitoring and alarm system for the mobile air supply cart.

As shown in FIG. 4, a pressure switch 32 is connected to the high pressure manifold 15 and is set to activate when the pressure of the air in the manifold drops below a predetermined amount (i.e., 500 psi), indicating that the amount of air remaining in the cylinder 6 supplying air to the manifold is running low. The output signal from the pressure switch 32 is directed, via conduit 33, to an electrical box 17 mounted on the frame 2. An audible alarm 38, shown in FIG. 5, is mounted on the frame 2 so as to be disposed between the cylinders 6 and is connected to the electrical box 17 so as to be activated by the pressure switch 32, ensuring that the presence of the low pressure indication does not go unnoticed. In addition, an on/off switch 19 and a test/reset button 18 are mounted on the electrical box 17, thereby allowing the audible alarm to be manually disabled, reactivated and tested.

Although the relatively simple monitoring and alarm system described above may be suitable in many applications, in some instances a more sophisticated monitoring and alarm system may be desirable to guard against the possibility that the operator may forget to flip the on/off switch 19 to the "on" position, thereby resulting in the monitoring and alarm being inoperable. Accordingly, FIG. 5 shows a schematic diagram of such a more sophisticated monitoring and alarm system. At the heart of the system is an electronic command module ("ECM") 60— comprising transistors, diodes, electronic reed switches, light emitting diodes, electronic timers and the like— that may be incorporated into the electrical box 17. In this embodiment, a single pole, double throw pressure differential switch is used for the pressure switch 32 so that, upon pressurization, the air 47 from the high pressure manifold 15 causes the normally open pole of the switch 32 to close and the normally closed pole open, thereby sending a signal 52 to the ECM 60 indicating that the system is operable. Thereafter, the ECM 60 checks the voltage of a battery 51 within the electrical box 17, via a signal 58, and, if appropriate, generates a signal 54 that activates a light emitting diode 48 on the face of the box, indicating that there is sufficient battery power for the operation of the ECM. Having received air pressure and battery voltage indications, the ECM 60 then generates a signal 55 that activates a second light emitting diode 49 on the box 17 notifying the operator that the system is operable.

Thereafter, if the ECM 60 receives a signal 53 from the pressure switch 32 indicating low pressure in the air 47, the ECM generates a signal 59 that activates an adjustable timer 61 that sounds the audible alarm 38 for a predetermined period of time. In addition, the ECM 60 also generates a signal 56 that activates a flashing third light emitting diode 50 on the box 17 that visually notifies the operator of a low pressure condition. After the predetermined period of time, the ECM 60 terminates the audible alarm 38 to conserve battery power but the third light emitting diode 50 continues to flash as long as the low pressure condition exists or until the test/reset button 18 is depressed, thereby generating a signal 57 to reset the ECM.

Referring again to FIG. 4, the three-way valve 27 allows the cylinder 6 that supplies air to the high pressure manifold 15 to be switched from one cylinder to the other. Thus, as one cylinder becomes exhausted, operation of the three-way valve 27 allows the exhausted cylinder to be isolated from the high pressure manifold 15, so that it can be replaced with a fresh cylinder, while simultaneously switching-in the unexhausted cylinder so that the supply of air to the user in not interrupted.

The piping system also features a coupling 28 connected, via a shut-off valve 26, to a second inlet port 31 in the high pressure manifold 15. The coupling 28 allows a remote source of air (not shown), such as an air compressor, to supply air to the user, through the high 15 and low 16 pressure manifolds and the pressure regulator 36, while simultaneously recharging the cylinders. During the recharging procedure, operation of the three-valve 27 allows each cylinder to be recharged sequentially.

Although the current invention has been described with reference to a system for supplying breathing air to a respirator mask for a fire fighter operating in a smoke-filled environment, the invention is also applicable to other situations in which a continuous source of breathing air is required— such as Hazardous Material Incidents or Haz Mat Site Monitoring. In addition, the invention is applicable for supplying compressed air to pneumatic tools, or for supplying other types of compressed gases to other types gas consuming devices, for use in emergency situations— such as automobile accidents. Moreover, although in the preferred embodiment the cart features two cylinders, a single cylinder or more than two cylinders could also be utilized. Thus, the current invention may be embodied in other specific forms without departing from the spirit or essential attributes thereof and, accordingly, reference should be made to the appended claims, rather than to the foregoing specification, as indicating the scope of the invention.

What is claimed:

1. A mobile air supply for supplying breathing air comprising:
 a) first and second compressed air cylinders; and
 b) an air supply cart for transporting said cylinders, said air supply cart having:
  (i) means for securing said cylinders to said air supply cart,
  (ii) an outlet port having means for placing a hose connected to a respirator mask in flow communication with said cylinders,
  (iii) means for receiving air from a source of compressed air remote from said air supply cart,
  (iv) means for selectively placing said outlet port in flow communication with either one of said cylinders while isolating the other one of said cylinders from said outlet port, said air supply cart directing air from one of said cylinders to a respirator mask, said means for placing said outlet port in flow communication with either one of said cylinders comprising means for simultaneously connecting said means for receiving air from a remote source to both one of said cylinders for charging said cylinder and to said outlet port for supplying a respirator mask, thereby permitting recharging of said cylinders without interrupting air supply to said user, and
  (v) means for reducing the pressure of said air delivered from said air cylinders to said outlet port placed in flow communication with and between said cylinders and said outlet port.

2. The mobile air supply according to claim 1, wherein said air supply cart further comprises at least one wheel rotatably coupled thereto to facilitate transporting said air supply cart.

3. The mobile air supply according to claim 2, wherein said air supply cart comprises a base to which said wheel is coupled and a frame to which said means for securing said cylinders to said air supply cart is mounted, said frame having means for being detached from said base.

4. The mobile air supply according to claim 3, wherein detaching means comprises a pin extending through said frame and said base.

5. The mobile air supply according to claim 1, wherein said means for placing said outlet port in flow communication with either one of said cylinders while isolating the other one of said cylinders from said outlet port further comprises:
 a) a high pressure manifold in flow communication with said cylinders and with said pressure reducing means; and
 b) a low pressure manifold in which said outlet port is disposed and in flow communication with said pressure reducing means.

6. The mobile air supply according to claim 5, wherein said means for placing said outlet port in flow communication with either one of said cylinders while isolating the other one of said cylinders from said outlet port further comprises:
 a) first and second hoses connected to said first and second cylinders, respectively; and
 b) a three-way valve connecting said high pressure manifold to each of said hoses.

7. The mobile air supply according to claim 5, wherein said means for receiving compressed air from a compressed air source remote from said cart comprises a coupling, said coupling in flow communication with said high pressure manifold.

8. The mobile air supply according to claim 5, further comprising a second outlet port disposed in said low pressure manifold, said second outlet port having means for placing a second hose connected to a second respirator mask in flow communication with said cart, whereby said cart is capable of simultaneous supplying breathing air to at least two respirator masks.

9. The mobile air supply according to claim 5, wherein said cart further comprises means for warning that the pressure of said air in said high pressure manifold has dropped below a predetermined value.

* * * * *